US00PP33547P3

(12) United States Plant Patent
Maillard et al.

(10) Patent No.: US PP33,547 P3
(45) Date of Patent: Oct. 12, 2021

(54) NECTARINE TREE NAMED 'CAKEPOP'

(50) Latin Name: ***Prunus persica* (L.) Batsch**
Varietal Denomination: CAKEPOP

(71) Applicant: AGRO SELECTIONS FRUITS, Elne (FR)

(72) Inventors: Laurence Maillard, Elne (FR); Arsène Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 46 days.

(21) Appl. No.: 16/602,671

(22) Filed: Nov. 20, 2019

(65) Prior Publication Data

US 2020/0178437 P1 Jun. 4, 2020

(30) Foreign Application Priority Data

Nov. 29, 2018 (QZ) ..... PBR 2018/3128

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 6/7454
See application file for complete search history.

(56) References Cited

PUBLICATIONS

Trademark to "Cake Pops", TESS, serial No. 90230686, filed Oct. 1, 2020.*

* cited by examiner

*Primary Examiner* — Anne Marie Grunberg
(74) *Attorney, Agent, or Firm* — Birch, Stewart, Kolasch & Birch, LLP

(57) ABSTRACT

A new and distinct variety of white flat nectarine tree denominated 'CAKEPOP' has fruits with high eating quality and very long shelf life without alteration before and after harvesting, with a semi-sweet white flesh, sometimes slightly greenish, and an attractive luminous skin with a very high percentage of luminous purple red blush on skin surface, on a red background.

5 Drawing Sheets

Botanical classification: *Prunus persica* (L.) Batsch.

Variety denomination: 'CAKEPOP'.

This application claims priority of Community plant variety right No. 2018/3128 filed on Nov. 29, 2018 (Nov. 29, 2018) which is hereby incorporated by reference in its entirety.

The new variety named 'CAKEPOP' is also known as 9C.10.07.15 NBPL or ASF17201. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'CAKEPOP', the provisional reference of this white flat nectarine tree variety was 9C.10.07.15 NBPL, corresponding to the tree 07 located in line 10 of the parcel 9C and selected during the year 2015. The letters "NBPL" are related to the first letters of the type of tree in French (NBPL for "Nectarine Blanche PLate", that means "white flat nectarine"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'CAKEPOP', the clone reference was 'ASF17201'.

BACKGROUND OF THE NEW VARIETY

The present invention relates to a new and distinct variety of white flat nectarine tree, *Prunus persica* (L.) Batsch, which has been given the variety denomination 'CAKEPOP'.

This new tree produces fruits with a long shelf life without alteration both on the tree after growth completion and after harvesting, very good eating quality, semi-clingstone white flesh fruits, slightly greenish, for fresh market in August or early in September in the Pyrénées-Orientales department, France.

ORIGIN OF THE VARIETY

The 'CAKEPOP' white flat nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'CAKEPOP' variety results from a pollinated cross between a white nectarine tree named 'NECTARLOVE' (U.S. Plant Pat. No. 23,419) which was used as a seed parent, or female parent, and the 'CAKEDELICE' (U.S. Plant Pat. No. 25,632) white flat nectarine tree which was used as the pollen parent, or male parent.

The 'CAKEPOP' variety was obtained by hybridizing and propagated by grafting on a 'INRA GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CAKEPOP' white flat nectarine tree blooms at the end of February or early in March near Elne in the Pyrénées-Orientales department, France. The blooming period is considered medium. However, it was observed that its late date of blooming seems to be highly dependant on climatic conditions.

The first fruit of 'CAKEPOP' ripens generally late in the season, during August or early in September. More particularly, it usually ripens between August $6^{th}$ and September $13^{th}$. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
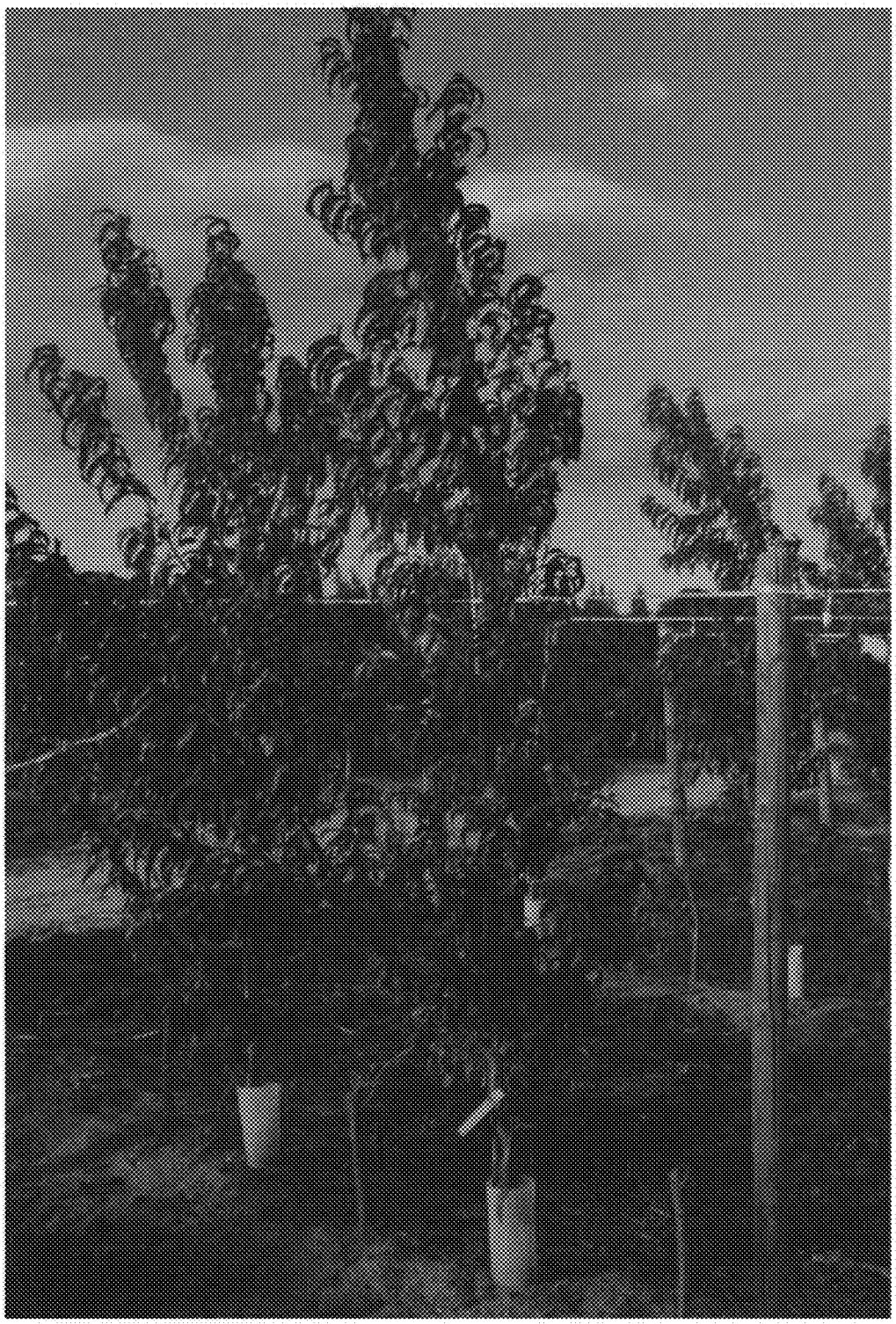
FIG. 1 is a color photograph that shows typical specimens of trees of the new variety 'CAKEPOP' in orchard, at ripening time, with branches bearing fruits.
Figure 2:
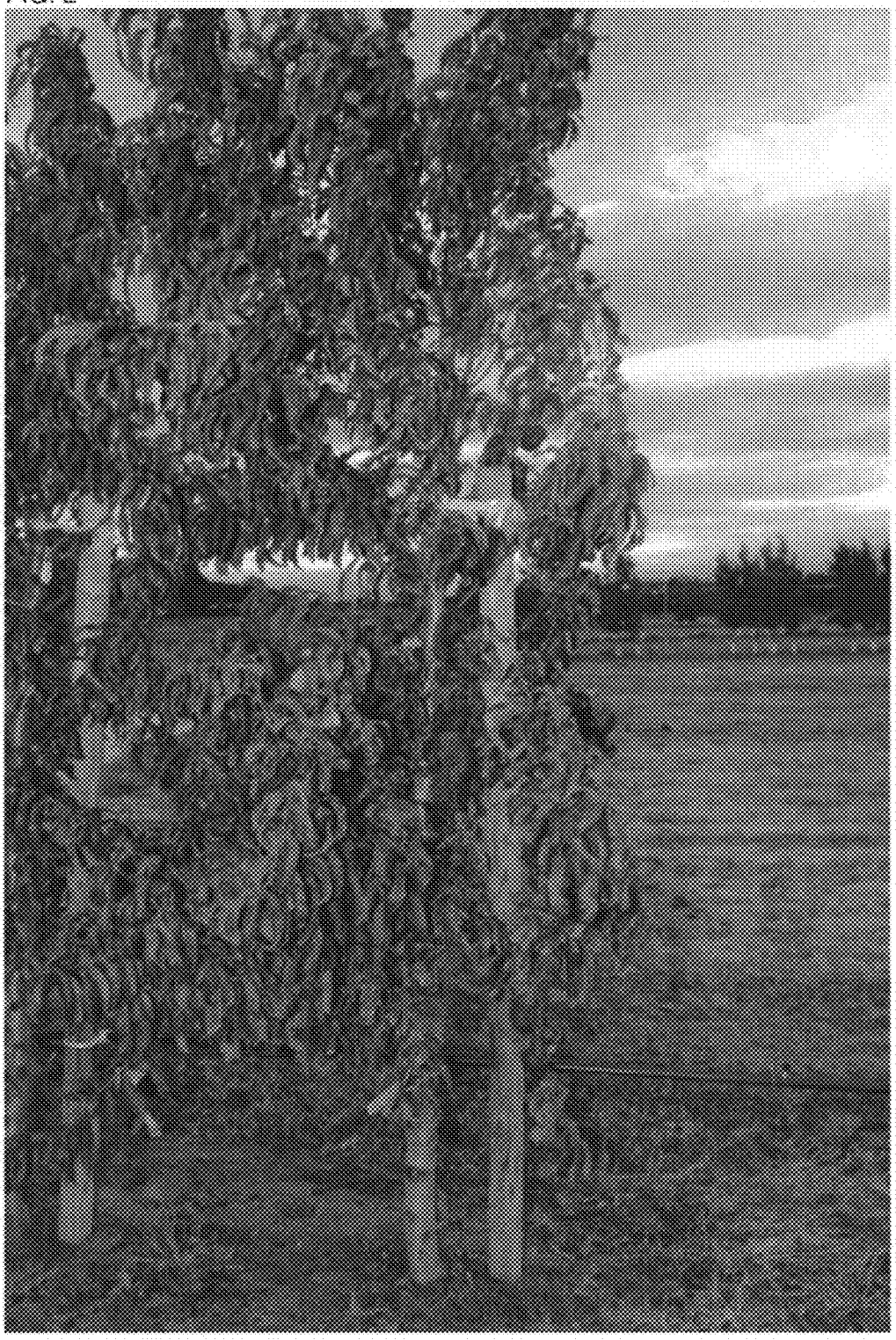
FIG. 2 is a second color photograph that shows typical specimens of trees of the new variety 'CAKEPOP' in orchard, at ripening time, with branches bearing fruits.
Figure 3:
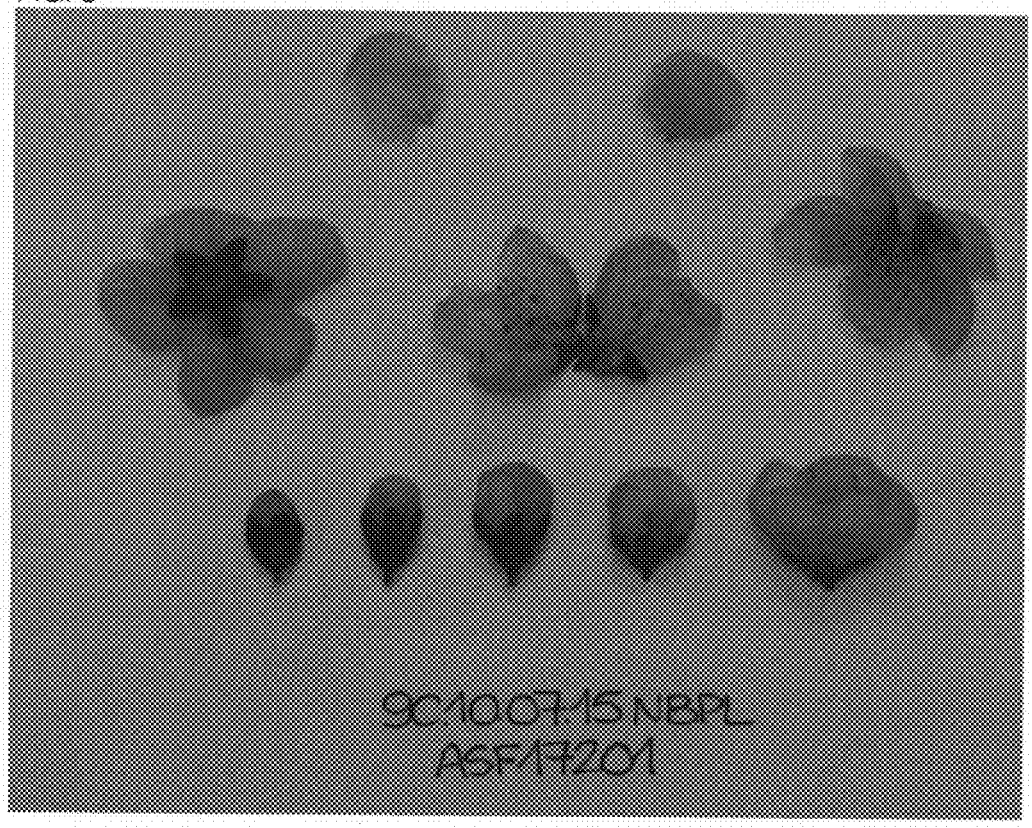
FIG. 3 is a color photograph which depicts the flower buds at different development stages, and the reverse and side views of the flower and the reproductive organs with petals removed, of the new variety 'CAKEPOP', which is also referenced '9C.10.07.15 NBPL ASF17201' by the breeder.
Figure 4:
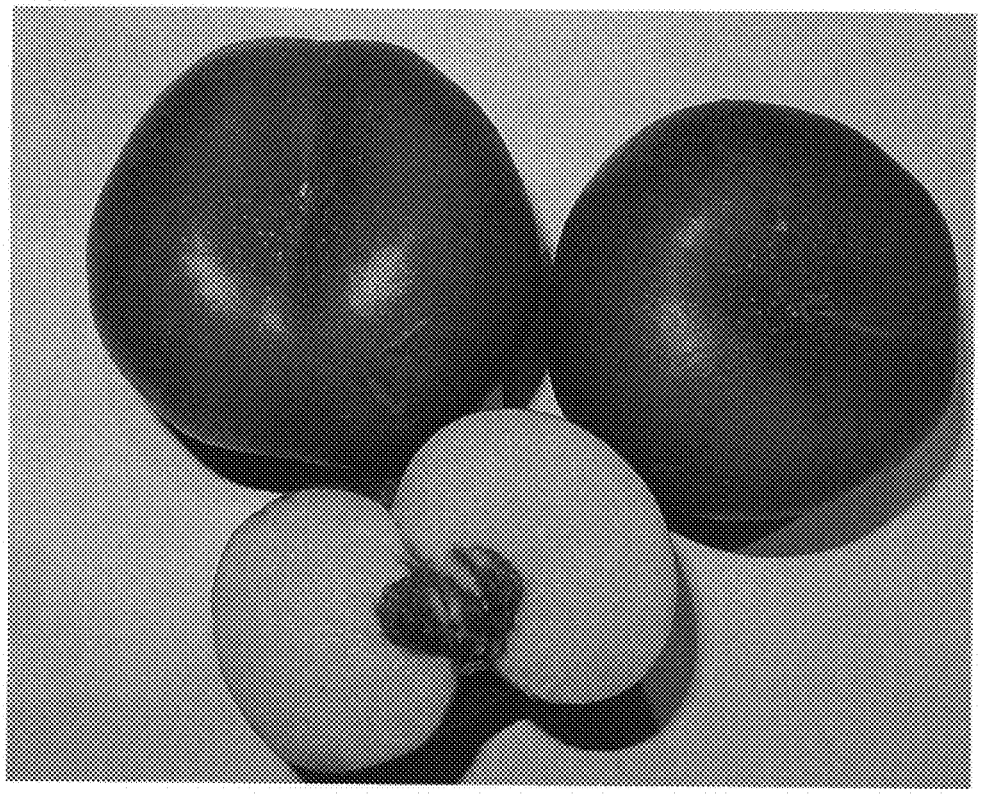
FIG. 4 is a color photograph that shows a close view of typical specimens of the fruit of the new variety 'CAKEPOP' at ripening time, one of these fruits having been cut with the stone left in the shown half.
Figure 5:
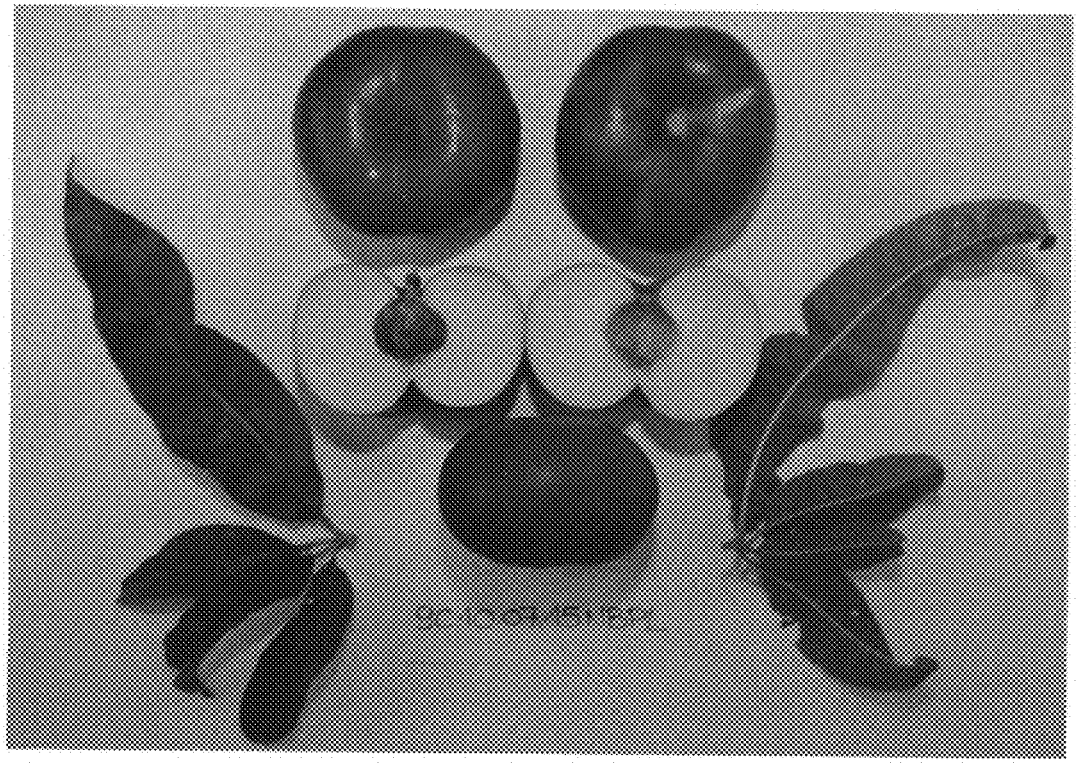
FIG. 5 is a color photograph which shows the upper and lower sides of leaves and different views of four typical specimens of the fruit, one having been cut in half with the stone being left in one of the halves for depicting leaves, fruit flesh, the stone and the stone cavity of the new variety.
Figure 6:
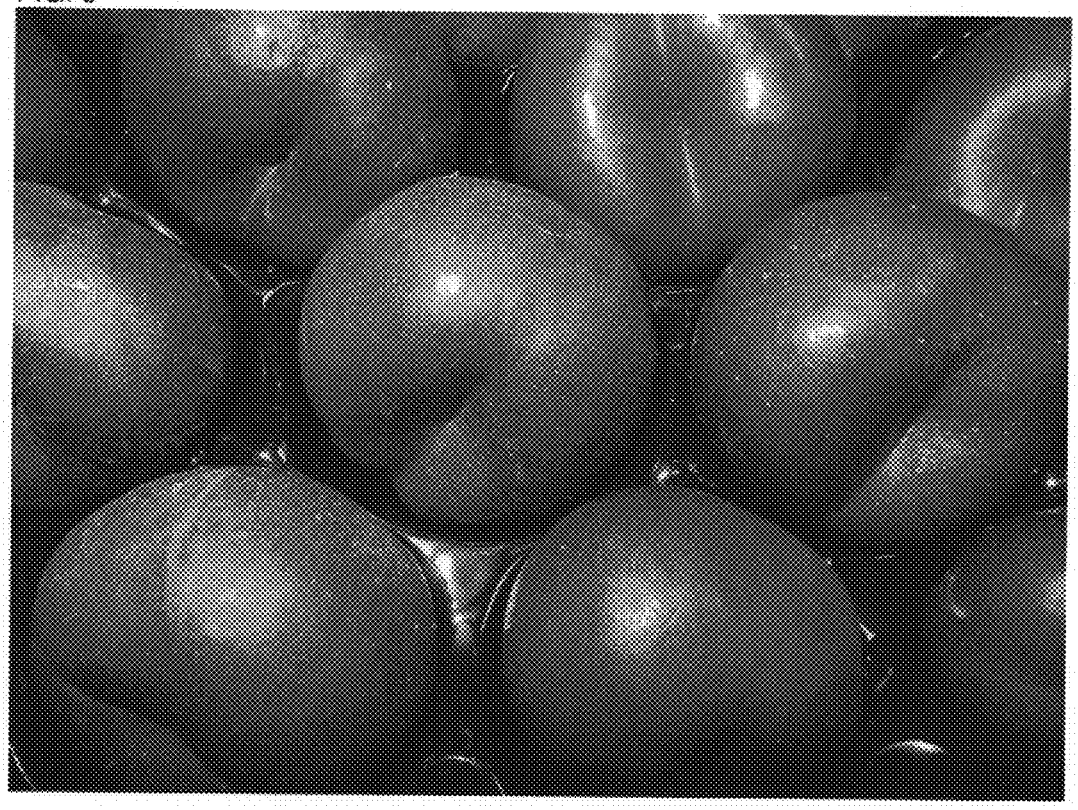
FIG. 6 is a color photograph that shows a close view of typical specimens of the fruit of the new variety 'CAKEPOP' at ripening time.
Figure 7:
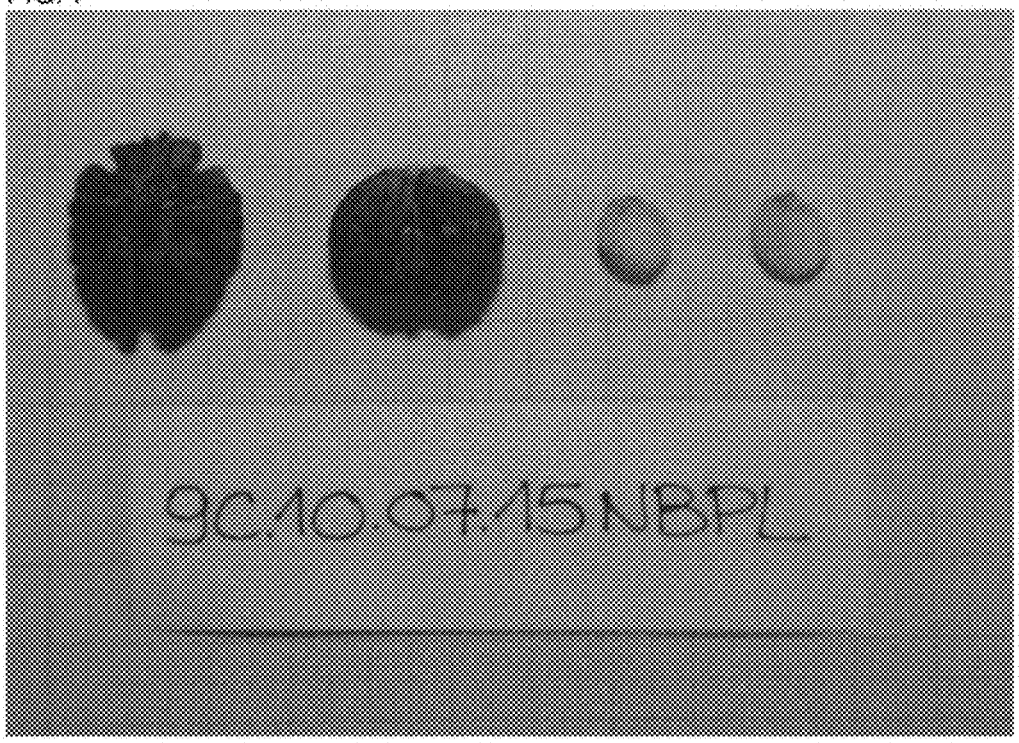
FIG. 7 is a color photograph showing different views of the stone of the new variety and the kernel of the stone.

The views of trees, leaves and fruits have been photographed in their third growing season (second year of production). The views of flowers have been photographed in their second growing season (first year of production).

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CAKEPOP' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered medium; flowering begins at the end of February or early in March. The type of flower is showy (rosette) with medium petal size. Petals are medium pink. Leaf glands are present and intermediate. The fruit flesh is white, sometimes slightly greenish, and generally without any red pigmentation. The fruit skin is medium thick, with a luminous purple red blush on a red background. The stone is semi-clingstone and its size is small. Fruit taste is semi-sweet, aromatic and with a high level of sugars.

Compared to 'CAKEAUGUST' white flat nectarine variety (not patented), the fruits of 'CAKEPOP' ripen approximately two days earlier. The fruits of the new variety 'CAKEPOP' are rounder than the fruits of 'CAKEAUGUST' and considered more or less symmetrical. The fruit skin of the new variety 'CAKEPOP' is colored with a luminous purple red blush covering 95% of the skin surface, on a red background. In comparison, the fruits of 'CAKEAUGUST' are less colored. The red blush covers 80 to 90% of the surface on a cream background. The pistil cavity is very well closed in the 'CAKEPOP' fruits, whereas the closing of the pistil cavity is incomplete on fruits of the 'CAKEAUGUST' variety. Finally, the fruits of the new variety 'CAKEPOP' have a long shelf life contrary to the fruits of the 'CAKEAUGUST' variety, having a medium shelf life.

Compared to 'NECTARLOVE' (U.S. Plant Pat. No. 23,419), the round white nectarine which was used as the seed parent as set forth above, the fruits of the new variety are flat in shape.

Moreover, the fruits of the new variety 'CAKPOP' ripen more than one month, sometimes one month and a half, later than the first fruits of 'NECTARLOVE'.

Compared to its pollen parent 'CAKEDELICE' (U.S. Plant Pat. No. 25,632) white flat nectarine, the fruits of the new variety 'CAKEPOP' also ripen later, usually 1 month later.

DETAILED DESCRIPTION

Referring more specifically to the pomological details of this new and distinct variety of white flat nectarine tree, the following was observed on trees in their third growing season (second year of production) for trees, leaves and fruit and on trees in their second growing season (first year of production) for the flowers under the ecological conditions prevailing at the orchards located near the town of Elne, Pyrénées-Orienteles departement, France. All observations have been done on rootstock cultivars. Used rootstocks were 'INRA GF677' (non-patented) trees. All major color code designations are by reference to The R.H.S. Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduced to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium.

*Productivity.*—Productive to very productive. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1-month ½ before harvesting flat fruits, significantly promotes fruit qualities, especially growth, color and firmness. Moreover, contamination risks due to *Monilia* or rot are significantly reduced. 'CAKEPOP' variety is not much sensitive to cracking of pistil cavity, to cork formation into peduncle cavity or to *Monilia.*

*Bearer.*—Very regular. The fruit distribution is considered homogenous on mixed branches and spurs having more than 1 year. Thinning of 2 fruits out of 3 was necessary for the tree valorisation. Thinning was necessary every year during the years of observation.

*Form.*—The 'CAKEPOP' variety has naturally a semi-flared to semi-upright shape.

*Density.*—Considered dense.

*Hardiness.*—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. Traditionally, flat fruits are more sensitive to critical low temperatures and to climatic variations, because of the flower morphology in which the ovule is less protected than in the classical round fruits. Thus, areas not much exposed to frost are recommended for trees growth. However, 'CAKEPOP' trees seem to be very resistant to critical frosty weather. Experimentations on the same orchard in Elne, Pyrénées-Orientales department, with winter chilling requirement below 7.2° C. comprised between 350 hours and 1200 hours according to the specificities of the year, 1031 hours in 2012-2013, 777 hours in 2013-2014, 893 hours in 2014-2015, 718 hours in 2015-2016, 825 hours in 2016-2017, 1017 hours in 2017-2018 and 844 hours in 2018-2019 showed a good behavior of the tree in all cases. No damages were caused by ascertained temperatures as low as −12 degrees Celsius in winter. The tree was also very resistant to frosty springtime weather.

Trunk:

*Diameter.*—Approximately 44.0 to 48.0 millimeters in diameter when measured at a distance of approximately 20.0 centimeters above the soil level in their third growing season (second year of production).

*Bark texture.*—Considered rough, with lenticels.

*Lenticels.*—Numerous lenticels are present. The number of lenticels reaches 2 lenticels per $cm^2$. The lenticels range in size from approximately 2.5 to 3.5 millimeters in width, and about 1.5 to 2.0 millimeters in height.

*Lenticel color.*—The lenticels have a grey color (RHS Grey 201 B).

*Bark coloration.*—The bark has a light brown to grey color (RHS Brown N 200 C or RHS Grey 201 A to RHS Grey 201 B).

Branches:

*Size.*—Mature branches and current season shoots are considered medium for the variety.

*Diameter.*—Average as compared to other nectarine varieties. The current season shoots have a diameter from 4.0 to 6.0 millimeters, and mature branches have a diameter from 7.0 to 9.0 millimeters.

*Surface texture.*—Average, wood which is several years old has no furrowed appearance.

*Crotch angles.*—Primary branches are considered variable, but the crotch angles are generally 45 degrees from the horizontal axis for current season shoots and 70 degrees from the horizontal axis for mature branches. This particular characteristic is not considered distinctive of the variety, however.

*Current season shoots.*—

*Internode length.*—Generally between 13.0 and 18.0 millimeters.

*Surface texture.*—Smooth.

*Color.*—The color of new shoot tips is considered light green (RHS Yellow Green 145 A) on lower part of new shoot tips, whereas the upper part is darker and colored in purple (RHS Greyed Purple 184 A).

*Mature branches.*—

*Internode length.*—Generally between 18.0 and 25.0 millimeters.

*Color of mature branches.*—Brown (RHS Grey Brown N199 B).

*Surface texture.*—The surface texture of mature branches is rough, with small lenticels.

*Lenticels.*—The number of lenticels on mature branches reaches 3 lenticels per $cm^2$. The lenticels range in size approximately 0.5 to 1.0 millimeter in height and approximately 1.0 to 1.5 millimeters in width. The lenticels are stretched round in shape.

*Lenticel color*.—The lenticels on mature branches have a light orange to beige color (RHS Greyed Orange 165 B or RHS Greyed Orange 165 C).

Leaves:

*Size*.—Considered medium for the species. The ratio leaf length/leaf width is 3.32.

*Leaf length*.—The leaf length is between 140.0 and 172.0 millimeters with leaf petiole. The medium length is 142.8 millimeters.

*Leaf width*.—The leaf width is between 37.0 and 47.0 millimeters. The medium width is 43.0 millimeters.

*Leaf form*.—Lanceolate.

*Leaf form* (*in cross section*).—Concave.

*Leaf base shape*.—Acute.

*Leaf tip form*.—Acute.

*Leaf thickness*.—Medium.

*Leaf color*.—

*Upper leaf surface*.—Green (RHS Yellow Green 147 A or RHS Green 137 A).

*Lower surface*.—A lighter green (RHS Yellow Green 146 A or RHS Yellow Green 147 B) than the upper leaf surface color.

*Leaf texture*.—Both upper and lower leaf surfaces are considered smooth and glabrous.

*Leaf venation*.—Pinnately veined.

*Mid-vein*.—

*Color*.—Light green, almost cream white (RHS Yellow Green 145 C or RHS Yellow Green 145 D). The color may evolve with maturity.

*Width*.—Approximately 1.50 millimeters.

*Leaf margins*.—

*Form*.—Leaf margins are considered crenate and slightly undulating.

*Uniformity*.—Leaves are isolated or grouped by 2 or 3. In this last case, one leaf of normal size is found with one or two smaller leaves (at least 50% smaller).

*Leaf petioles*.—

*Size*.—Considered medium.

*Length*.—About 11.0 to about 14.0 millimeters.

*Diameter*.—About 1.7 to 2.0 millimeters.

*Shape*.—Grooved.

*Petioles color*.—

*Upper petiole surface*.—Green (RHS Yellow Green 144 A or RHS Yellow Green N144 C).

*Lower surface*.—Light green (RHS Yellow Green 145 B).

*Leaf glands*.—

*Size*.—Considered medium. Their length is about 1.5 to 2.0 millimeters and their width is about 1.0 millimeter.

*Number*.—Generally 2 glands per leaf, sometimes 3.

*Type*.—Intermediate, between round and reniform.

*Margins*.—Smooth and regular.

*Position*.—Alternate on the upper part of petiole.

*Color*.—On young leaves, the leaf gland color is light green (RHS Green 145 B). On older leaves, leaf glands color is considered dark brown (RHS Grey Brown 199 A or RHS Grey Brown 199 B or RHS Brown 200 A).

*Leaf stipules*.—

*Generally*.—No leaf stipules were observed. But as seen in the characteristic relative to the leaves uniformity, it is possible to find leaves by groups of 2 or 3, with a normal-size leaf and smaller ones.

Flowers:

*Flower buds*.—

*Generally*.—At pre-floral stage of development, the floral buds are round in form with a round tip. Their form is evolving until blooming, with variables dimensions. Just before blooming, floral buds are approximately 9.0 to 10.0 millimeters wide and approximately 18.0 to 20.0 millimeters long. The distribution of the flower buds is homogeneous on trees.

*Color*.—This characteristic is dependent upon the proximity to bloom. At pre-floral stage of development (stage A), the bottom of the flower buds, or calyx, or flower receptacle, is of purple color at the outer surface of the calyx (RHS Greyed Purple 187 A or RHS Greyed Purple 187 B). The inner surface of the calyx is considered orange yellow (RHS Yellow Orange 23 A to RHS Yellow Orange 23 B). Above the calyx, the corolla, formed by the petals, is generally of pink color (RHS Red Purple 65 A) on both faces. Petal color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins at the end of February or early in March. The first bloom was observed on Feb. 29, 2016.

*Blooming time*.—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus, the full bloom was observed in 2016, from February 29$^{th}$ until March 9$^{th}$, then from March 3$^{rd}$ until Mar. 10, 2017 and then from February 22$^{nd}$ until Mar. 2, 2018.

*Duration of bloom*.—Approximately between 8 to 10 days. This characteristic varies slightly with the prevailing climatic conditions.

*Flower type*.—The variety is considered to have a showy (rosette) type flower. The fragrance is soft to moderate.

*Flower size*.—Considered medium. Flower diameter at full bloom is approximately 36.0 to 41.0 millimeters.

*Bloom quantity*.—Considered abundant, approximately between 35 and 40 flowers per meter, with a high rate of fruit set. The bloom is homogeneously distributed on the tree.

*Flower bud frequency*.—Generally 2 flower buds appear per node, occasionally 1.

*Petal size*.—

*Generally*.—Considered medium.

*Length*.—Generally between 20.0 and 22.0 millimeters.

*Width*.—Generally between 21.0 and 23.0 millimeters.

*Petal form*.—Round-shaped.
*Petal count*.—Generally 5.
*Petal arrangement*.—Overlapping.
*Petal texture*.—Smooth.
*Petal color*.—Both surfaces of the petal are colored with a pink to medium pink (RHS Red Purple 65 A) when young, becoming slightly darker until the end of blooming.
*Petal margins*.—Slightly undulating.
*Fragrance*.—Sweet.
*Petal claw*.—
*Form*.—The claw is considered to have a narrow form.
*Length*.—About 1.5 to 2.0 millimeters.
*Width*.—About 1.5 millimeters at the base.
*Color*.—A darker pink than the petal color (RHS Red Purple 58 A).
*Petal apex*.—
*Generally*.—The petal apices are generally wide dome-shaped.
*Flower pedicel*.—
*Length*.—Considered medium and having an average length of approximately 2.5 to 4.0 millimeters.
*Diameter*.—Considered average, approximately 1.25 to 1.75 millimeters.
*Color*.—Green (RHS Yellow Green 144 A to RHS Yellow Green 144 B).
*Calyx*.—
*Internal surface texture*.—Smooth.
*Color*.—At the stage F of blooming, when the flower is open, the inner surface of the calyx, or flower receptacle, is greenish yellow (RHS Yellow Green 153 D) or yellow orange (RHS Greyed Orange 163 B). The outer surface of the calyx is considered of purple-color (RHS Greyed Purple 187 A or RHS Greyed Purple 187 B).
*Sepals*.—
*Sepal count*.—Usually 5.
*Surface texture*.—The outer surface has a smooth texture.
*Margins*.—Smooth.
*Size*.—Medium.
*Length*.—Approximately 5.0 to 6.5 millimeters.
*Width*.—Approximately 4.5 to 5.5 millimeters.
*Form*.—Conic with a round tip.
*Color*.—The upper surface of sepals shows a purple color (RHS Greyed Purple 187 A or RHS Greyed Purple 187 B) whereas the lower surface is greenish (RHS Yellow Green 146 A or RHS Yellow Green 146 B).
*Average number of stamens per flower*.—Approximately 29 to 35 stamens per flower.
*Position of the stamen relative to the petals*.—The stamen is shorter than the petals.
*Anthers*.—
*Generally*.—Medium in length.
*Color*.—Anthers are colored with a red (RHS Red 46 A) or a yellow color (RHS Yellow Orange 17 C) depending on the maturity stage.
*Shape*.—Cordate.
*Pollen production*.—Pollen is abundant and has a yellow color (RHS Yellow 11 A or RHS Yellow 11 B) which may evolve with maturity. The present variety is considered auto-fertile (self-pollinating).
*Filaments*.—
*Size*.—Medium length, between 15.0 and 16.0 millimeters in length. Filaments length is generally higher than the pistil's length, or equal to the pistil's length.
*Color*.—Considered white (RHS White N155 D) to pink (RHS Red Purple 63 D) depending on the maturity stage. The color becomes darker during the blooming.
*Pistil*.—
*Number*.—Usually 1.
*Generally*.—Average in size.
*Length*.—Approximately 16.0 to 17.0 millimeters including the ovary. Generally smaller than the stamen length, or equal to the stamen length.
*Color*.—Considered green (RHS Yellow Green 145 A or RHS Yellow Green 145 B) to yellowish (RHS Yellow Green 151 D) depending on the maturity stage of the flower. The color evolves during the blooming.
*Stigma*.—Approximately 1.0 millimeter in diameter, with a yellowish color (RHS Yellow Green 153 C to RHS Yellow Green 153 D).
*Ovary*.—
*Height*.—Approximately 1.5 to 2.0 millimeters.
*Diameter*.—Approximately 1.5 to 2.0 millimeters.
*Color*.—Green (RHS Yellow Green 145 A).

Fruit:
*Maturity when described*.—Very firm in ripe conditions (shipping ripe).
*Date of first picking*.—Aug. 16, 2015.
*Date of last picking*.—The date of harvest varies slightly with the prevailing climatic conditions. The 'CAKEPOP' variety has a late date of picking, and a grouped maturity. The maturity is grouped within 7 to 8 days and the harvest is generally performed in two runs. Last known picking times carry on from August 16$^{th}$ to Aug. 23, 2015, then from August 15$^{th}$ to Aug. 21, 2016, then from August 6$^{th}$ to Aug. 12, 2017 and then from September 6$^{th}$ to Sep. 13, 2018.
*Size*.—
*Generally*.—Homogeneous in size, size 2A or A. Considered medium to large.
*Average cheek diameter*.—Approximately 63.0 to 71.0 millimeters.
*Average axial diameter*.—Approximately 40.0 to 46.0 millimeters.
*Typical weight*.—Generally about 115.0 to 150.0 grams. This characteristic is high dependent upon the prevailing cultural practices, and therefore is not particularly distinctive of the variety.
*Fruit form*.—
*Generally*.—Round and flattened. The fruit is generally uniform in symmetry, viewed from the suture's plane. The surface of the fruit is regular.
*Suture*.—
*Fruit suture*.—The suture is absent, or wide-mouthed and slightly marked when present, extending from the base to the apex. No apparent callousing or stitching exists along the suture line. Not pointed.
*Color*.—The suture has generally a similar color to the whole fruit color, a luminous purple red (RHS Greyed Purple 187 A).
*Base*.—
*Mucron*.—Absent.
*Closing of the pistil cavity*.—Very good.
*Ventral surface*.—

*Form*.—Smooth.
*Apex*.—Slightly depressed.
*Base*.—Semi-flared, shallow.
*Stem cavity*.—Average depth of the stem cavity is considered medium, about 7.0 to 9.0 millimeters. Average width is about 14.0 to 16.0 millimeters.
*Fruit skin*.—
*Thickness*.—Considered medium thick and strong, and the adherence of skin to flesh is strong to medium, depending on the fruit maturity.
*Texture*.—Smooth and glabrous, without any pubescence.
*Taste*.—Semi-sweet.
*Tendency to crack*.—None observed.
*Color*.—
*Blush color*.—This blush color is a luminous purple red (RHS Greyed Purple 187 A). The purple red blush covers 95 to 100% of the fruit skin surface on a red background (RHS Greyed Purple 183 A or RHS Greyed Red 180 A) covering at the most 5% of the fruit skin surface. The percentage of the blush on the fruit skin surface can vary and is generally dependant upon the prevailing conditions under which the fruit was grown.
*Ground color*.—The ground color covers at the most 5% of the fruit skin surface, and is considered orange red (RHS Greyed Purple 183 A or RHS Greyed Red 180 A).
*Lenticels*.—None.
*Fruit stem*.—Medium in length, approximately 6.0 to 9.0 millimeters.
*Diameter*.—Approximately 4.0 to 5.0 millimeters.
*Color*.—Pale green (RHS Yellow Green 145 A).
*Flesh*.—
*Ripens*.—Very homogenously, slowly. The flesh has a long shelf life.
*Texture*.—Firm to very firm, very dense, crunchy, melting at harvest maturity stage.
*Fibers*.—Not fibrous.
*Aroma*.—Present to very pronounced.
*Eating quality*.—Considered semi-sweet, very good, aromatic and sugary.
*Flavor*.—Considered semi-sweet. The Brix is generally comprised between 15.5 and 16.0.
*Juice*.—Juicy at complete maturity.
*Brix*.—Generally comprised between 15.5 and 16.0 degrees. This characteristic varies slightly with the number of fruit per tree; prevailing cultural practices; and the surrounding climatic conditions.
*Flesh color*.—White flesh (RHS White 157 D), or white flesh slightly greenish (RHS Green White 155 D), usually without any red pigmentation.

Stone:
*Type*.—Semi-Clingstone, more or less semi-adherent depending on the fruit maturity.
*Size*.—Considered small for the variety. The stone size varies significantly depending upon the tree vigor, crop load and prevailing growing conditions.
*Length*.—Approximately 15.0 to 16.0 millimeters.
*Width*.—Approximately 23.0 to 24.0 millimeters.
*Diameter*.—Approximately 20.0 to 21.0 millimeters.
*Form*.—Flattened.
*Base*.—Straight.
*Apex*.—
*Shape*.—The stone apex is flattened.
*Stone cavity*.—Considered small, with flattened form and dimensions corresponding to the stone's dimensions.
*Stone surface*.—
*Surface texture*.—The pit is transversely furrowed on its entire surface. Furrows are deeper and more oblate on lateral sides.
*Ridges*.—The surface texture is generally characterized by more prominent ridges along the ventral edges and at the apical tip.
*Ventral edge*.—
*Width*.—Narrow, approximately 3.0 millimeters at mid-suture.
*Dorsal edge*.—
*Shape*.—Grooved.
*Stone color*.—The color of the dry stone is generally considered brown (RHS Greyed Orange 165 C or RHS Greyed Orange 165 D).
*Tendency to split*.—Splitting is absent.
*Kernel*.—
*Size*.—The kernel is considered small.
*Shape*.—Elliptic flattened, sometimes double.
*Length*.—Approximately 9.0 to 10.0 millimeters.
*Width*.—Approximately 9.0 to 10.0 millimeters.
*Thickness*.—Approximately 9.0 to 10.0 millimeters.
*Pellicle*.—The pellicle of the kernel has a short pubescence.
*Color*.—The kernel skin is light orange yellow colored (RHS Greyed Yellow 162 A). The almond, which is the seed of the kernel, is white (RHS White 155 B) and has a sweet tasting. The kernel and its embryo are mature at the time of fruit maturity.
*Use*.—The subject variety 'CAKEPOP' is considered to be a white flat nectarine tree of the late season of maturity, and which produces fruits that are considered firm, attractively colored with a very luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.
*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.
*Shipping quality*.—Considered very good. The fruit of the new white flat nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.
*Resistance to insects and disease*.—No particular susceptibilities were noted. The present variety is not very sensitive to Monilia or rot. The pistil cavity is completely closed, generally without any cork formation.

Although the new variety of white flat nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of white flat nectarine tree as illustrated and described, characterized by fruits with high eating quality and very long shelf life without alteration before and after harvesting, with a semi-sweet white flesh, sometimes slightly greenish, and an attractive luminous skin with a very high percentage of luminous purple red blush on skin surface, on a red background.

* * * * *